United States Patent [19]

Matsui et al.

[11] Patent Number: 4,504,422
[45] Date of Patent: Mar. 12, 1985

[54] PROCESS FOR PRODUCING AN ACETAL

[75] Inventors: Kanenobu Matsui; Shinichiro Uchiumi; Akira Iwayama; Takashi Umezu, all of Ube, Japan

[73] Assignee: Ube Industries, Ltd., Yamaguchi, Japan

[21] Appl. No.: 475,754

[22] Filed: Mar. 16, 1983

Related U.S. Application Data

[63] Continuation of Ser. No. 333,110, Dec. 21, 1981, abandoned.

[30] Foreign Application Priority Data

Dec. 23, 1980 [JP] Japan ................................ 55-181332
Dec. 23, 1980 [JP] Japan ................................ 55-181333
Jul. 30, 1981 [JP] Japan ................................ 56-118410

[51] Int. Cl.$^3$ ..................... C07C 41/50; C07C 120/00
[52] U.S. Cl. ................................. 260/465.6; 568/391; 568/458; 568/591; 568/592; 568/594; 568/596; 560/186; 562/587; 564/201
[58] Field of Search ............... 568/591, 592, 594, 596, 568/391, 458; 260/465.6; 560/186; 562/587; 564/201

[56] References Cited

U.S. PATENT DOCUMENTS 3,236,897  2/1966  Hornig et al. ...................... 568/401
3,285,970 11/1966  Schaeffer ............................ 568/594
3,290,362 12/1966  Schaeffer ........................ 568/594 X
3,346,623 10/1967  Young ............................. 568/594 X

OTHER PUBLICATIONS

Moiseev et al., Acad. Sci. U.S.S.R. Doklady Chem. Section (1960), 801–804.

Primary Examiner—Bernard Helfin
Attorney, Agent, or Firm—Finnegan, Henderson, Farabow, Garrett & Dunner

[57] ABSTRACT

An acetal is produced at a high yield and a high selectivity by contacting an olefin and an alcohol with each other in the presence of (a) a nitrite, (b) a platinum group metal or the salts thereof and (c) a halide at a high reaction rate without requirement of any troublesome operations for the separation, recovery and regeneration of the catalyst.

10 Claims, No Drawings

PROCESS FOR PRODUCING AN ACETAL

This is a continuation of application Ser. No. 333,110 filed Dec. 21, 1981 and now abandoned.

The present invention relates to a process for producing an acetal and, more specifically, it relates to a process for producing an acetal from an olefin and an alcohol.

Acetals can be applied in various ways industrially as starting materials for the synthesis of organic solvents, perfumes and agricultural chemicals, and can be converted to vinyl ether, which is a starting material for producing watersoluble polymers by the removal of alcohol, and the like.

Heretofore, acetals have been industrially produced by, for example, the reaction of an alcohol with an aldehyde or the oxidation of an alcohol with manganese dioxide and sulfuric acid.

Also known in the art are various methods for producing acetals by reacting olefins, alcohols and oxygen in the presence of platinum metal catalysts.

However, the above-mentioned methods for the production of acetals present problems from an industrial point of view in that the reaction rate is low. The yield of and the selectivity to the desired products are not good, and the catalyst systems are complicated, and the operations for the separation, recovery and regeneration thereof are troublesome. Therefore, these methods have not yet been used as an industrial process.

Accordingly, an object of the present invention is to obviate the above-mentioned problems concerning the prior methods for producing an acetal and to provide a process for producing an acetal from an olefin and an alcohol.

Another object of the present invention is to provide a process for producing, at a high yield and a high selectivity, an acetal from an olefin and an alcohol at a high reaction rate without the requirement of any troublesome operations for the separation, recovery and regeneration of the catalyst.

Other objects and advantages of the present invention will be apparent from the following description.

In accordance with the present invention, there is provided a process for producing an acetal comprising the step of contacting an olefin and an alcohol with each other in the presence of (a) a nitrite (i.e. an ester of nitrous acid), (b) at least one component selected from the group consisting of platinum group metals and the salts thereof and (c) at least one halide (or halogenide).

Typical examples of olefins used as a starting material in the present invention are: aliphatic olefins such as ethylene, propylene, butene, isobutylene and the like; olefin aldehydes such as acrolein, crotonaldehyde and the like; olefin ketones such as methyl vinyl ketone, ethylidene acetone, allyl methyl ketone and the like; olefin nitriles such as acrylonitrile, methacrylonitrile, crotononitrile and the like; olefin carboxylic acids and the esters thereof such as acrylic acid, methacrylic acid, crotonic acid, cinnamic acid and the like; olefin amides such as acrylamide, methacrylamide and the like; alicyclic olefins such as cyclopentene, cyclohexene, cycloheptene and the like; and styrene.

Typical examples of alcohols also used as a starting material in the present invention are aliphatic alcohols having 1 to 12 carbon atoms such as methanol, ethanol, n- or i-propanol, n- or i-butanol, sec-butanol, n- or i-heptanol, n- or i-octanol, n- or i-decanol, n- or i-dodecanol and the like. These alcohols may be substituted with any substituents such as an alkoxyl group, a halogen atom, a phenyl group and the like as long as these substituents do not adversely affect the desired reaction.

Typical examples of nitrites also used in the present invention are those derived from the above-mentioned alcohols and nitrous acid. Such examples are methyl nitrite, ethyl nitrite, propyl nitrite, butyl nitrite, amyl nitrite, hexyl nitrite, heptyl nitrite, nonyl nitrite, decyl nitrite, tridecyl nitrite, hexadecyl nitrite, benzyl nitrite and the like.

These nitrites can be generally used in an amount of 0.01% by weight or more, preferably 0.1% through 20% by weight, based on the amount of the starting alcohol in the case where the reaction is carried out in a liquid phase. In the case where the amount of the nitrites is less than 0.01% by weight, the production yield and the production rate of the desired acetal tend to be decreased.

In the case where the reaction is carried out in a vapor phase, the ratio of the olefins, the alcohols and the nitrites in the vapor phase is approximately 5–25% by volume: 5–25% by volume: 1–30% by volume, although the ratio can vary widely.

The nitrites can be previously charged into a reaction system, or can be introduced into a reaction system in such a form that the nitrites are diluted with an inert gas such as nitrogen gas, carbon dioxide gas or the like, in the case where the reaction is carried out in a liquid phase. In the case where the reaction is carried out in a vapor phase, the nitrites can be charged alone into a reaction system or can be charged into a reaction system in a mixture with the olefins and/or the alcohols and, generally, can be charged into a reaction system in such a form that the nitrites are diluted with an inert gas, such as, nitrogen gas, carbon dioxide gas or the like.

Instead of the nitrites, nitrogen oxides or the hydrates thereof can be charged, optionally together with oxygen, into a reaction system, whereby the nitrites can be formed by the reaction thereof with the alcohols in the reaction system.

The platinum group metals and the salts thereof used as a catalyst in the present invention include, for example, palladium, platinum, rhodium, ruthenium iridium and osmium and the halides, sulfates, nitrates, phosphates and acetates thereof. These catalysts can be used, together with an adequate amount of other metals such as gold, vanadium, molybdenum and the salts thereof.

The catalysts can be used in a concentration of 1 ppm through 10% by weight, preferably 100 through 1000 ppm, in terms of the platinum metal, in the reaction liquid in the case where the reaction is carried out in a liquid phase.

In carrying out the present invention, the catalysts can be desirably supported, together with the co-catalysts mentioned below, on a suitable carrier such as activated carbon, silica gel, alumina, silica-alumina, silicon carbide, diatomaceous earth, magnesia, pumice stone, molecular sieves and the like, in order to facilitate the recovery of the catalysts and/or the desired products from the reaction mixture and also to prevent the loss of the catalysts. Although there is no critical limitation regarding the amount of the catalyst supported on the carrier, the amount of the catalyst, in terms of platinum group metal, is desirably 0.01% by weight or more and, more desirably, 0.1 through 1.0% by weight, based on the weight of the carrier.

The halides (or halogenides) used as a co-catalyst in the present invention can be any compounds which contain halogen atoms (i.e. F, Cl, Br, I). Typical examples of the halides which can be desirably used in the present invention are: hydrogen halides; the halides of platinum metals such as palladium, platinum, rhodium, and iridium; the halides of alkali metals such as sodium, potassium and lithium; the halides of alkaline earth metals such as calcium and magnesium; the halides of copper such as copper chlorides, copper bromides and copper iodides; the halides of iron such as $FeCl_2$, $FeCl_3$, $FeCl_2.4H_2O$, $FeCl_3.6H_2O$ and $FeBr_3$; and the halides of the other metals or non-metals such as cobalt, zinc, nickel, aluminum, molibdenum tin, manganese, chronium, antimony and the like.

These halides can be desirably used in an amount of 0.1 through 10, more desirably 0.5 through 5, and, most desirably, 0.5 through 2, in terms of an atomic number of a halogene atom, based on the platinum group metal, in view of the increasein the yield of and the selectivity to the desired product. In the case where the halide of the platinum metal is used as the catalyst in the present invention, the halide is not necessarily present in the reaction mixture.

In the case where the present reaction is carried out in a vapor phase, iron compounds, other than the halides of iron, such as $Fe_2O_3$, $Fe_3O_4$, $Fe(OH)_3$, $FeCO_3$, $Fe_2(SO_4)_3$ and $Fe(NO_3)_3.9H_2O$ can be desirably used, in addition to the above-mentioned halides. The amount of the iron compounds is 0.1 through 10, desirably 0.5 through 5, in terms of an atomic number of an iron metal, based on the platinum group metal.

The reaction can be carried out in the presence of, or in the absence of, an inert solvent. Examples of such inert solvents are: the esters of lower fatty acids such as ethyl acetate, propyl acetate, butyl acetate, amyl acetate, ethyl propionate, butyl propionate, methyl lactate, ethyl lactate, propyl lactate, butyl lactate and the like; the esters of aliphatic dicarboxylic acid such as dimethyl oxalate, diethyl oxalate, dipropyl oxalate, dibutyl oxalate, dimethyl succinate, diethyl succinate, dimethyl adipate and the like; carbonic acid diesters such as dimethyl carbonate, diethyl carbonate, dipropyl carbonate, dibutyl carbonate and the like; the esters of aromatic carboxylic acids such as methyl benzoate, ethyl benzoate, dimethyl phthalate and the like; ethers such as dioxane, dibutyl ether and the like; hydrocarbons such as benzene, toluene, xylene, cyclohexane, n-hexane and the like; and the other solvents such as monochlorobenzene, dichlorobenzene, nitrobenzene, acetophenone, alkylsulfone, alkylsulfoxide and the like.

Furthermore, the production rate of the acetal can be further increased by the addition of oxygen in an amount of, for example, 0.1 through 10% by volume in a feed gas. In the case where, as mentioned hereinabove, the reaction is carried out, while introducing the nitrites into a reaction vessel, the oxygen can be introduced as a mixture thereof with the nitrites.

The present reaction can be desirably carried out in a liquid phase at a temperature of 20° through 150° C. under an atmospheric pressure or under pressure, for example, up to 200 kg/cm G.

The present reaction can be desirably carried out at a temperature of 50° through 200° C. under an atmospheric pressure or under pressure, for example, up to 20 kg/cm G, in the case where the reaction is carried out in a vapor phase. The starting gaseous materials can be desirably contacted with a catalyst layer or bed at a space velocity (S.V.) of 500 through 5000/Hr.

The present invention will now be further illustrated by, but is by no means limited to, the following Examples and comparative Examples.

EXAMPLE 1

Into a four-necked flask provided with a gas feed pipe, an olefin feed pipe, a thermometer and a reflux condenser, 50 ml of n-butanol and 0.1 g of palladium chloride were charged. The contents in the flask were maintained at a temperature of approximately 86° C. 5.3 g of acrylonitrile was added to the flask with stirring over 50 minutes, while a nitrogen gas containing 12% by volume of n-butyl nitrite was introduced into the flask at a rate of 210 ml/min. over 60 minutes. The effluent gas discharged from the top of the reflux condenser was introduced into a trap containing 50 ml of n-butanol, which was cooled by a dry ice-methanol bath, whereby the reaction products were collected.

The reaction products in the flask and the butanol trap were analyzed by means of gas chromatography. As a result, 27.4 m mol of cyanoacetaldehyde di n-butylacetal was produced and, as a by-product, only trace amounts of $C_4H_9OCH=CHCN$ were formed.

EXAMPLES 2-5

Reactions were carried out in a manner as described in Example 1, except that the liquid composition at the beginning of the reaction, and the feed rate of nitrogen gas containing n-butyl nitrite were changed as shown in Table 1 below.

The results thus obtained are shown, together with results of Example 1, in Table 1 below.

TABLE 1

| Example | Feed Rate of Nitrogen Gas Containing n-Butyl Nitrate (ml/min.) | Liquid Composition at beginning of Reaction (ml) | | Yield of Cyanoacetaldehyde Di n-Butyl-Acetal (m mol) |
|---|---|---|---|---|
| | | n-Butyl Nitrite | n-Butanol | |
| 1 | 210 | 0 | 50 | 27.5 |
| 2 | " | 10 | 40 | 39.0 |
| 3 | 100 | 0 | 50 | 15.8 |
| 4 | " | 10 | 40 | 25.8 |
| 5 | None | " | ' | 15.2 |

EXAMPLE 6

Into a flask provided with an agitator, 1400 ml of methanol, 600 ml of acrylonitrile and 1.2 g of palladium chloride were charged and the contents in the flask were maintained at a temperature of 63° C. 220 l/hr of a circulating gas was continuously charged into the flask with stirring. Said circulating gas was obtained by passing a gas discharged from the outlet of the flask, together with 7-8 l/hr of oxygen, through a methanol liquid, and contained 44% by volume of methyl nitrite and 45% by volume of nitrogen monoxide.

- As a result, the space time yield of cyanoacetaldehyde dimethylacetal was 25 g/l.hr at 6 hours after the beginning of the reaction.

EXAMPLE 7

The reaction was carried out in a manner as described in Example 3, except that air containing 12% by volume of n-butyl nitrite was fed at a rate of 100 ml/min. in lieu of the nitrogen gas containing 12% by volume of n-butyl nitrite.

As a result, 46.3 m mol of cyanoacetaldehyde di n-butylacetal was formed.

COMPARATIVE EXAMPLE 1

The reaction was carried out in a manner as described in Example 3, except that air was fed into a flask at a rate of 90 ml/min. in lieu of the nitrogen gas containing 12% by volume of n-butyl nitrite.

As a result, no formation of acetal was observed.

EXAMPLES 14-18

Into the four-necked flask used in Example 1, 50 ml of methanol, a given amount of an olefin and 0.1 g of palladium chloride were added. The contents in the flask were maintained at the temparature listed in Table 3 below (i.e. the reaction temperature) and a nitrogen gas containing 8% by volume of methyl nitrite was fed into the flask at a rate of 200 ml/min. for the time shown in Table 3 below (i.e. the reaction time).

TABLE 3

| Example | Olefins (m mol) | Temperature (°C.) | Reaction Time (hr) | Formed Acetal (m mol) |
|---|---|---|---|---|
| 14 | Cyclohexene (100) | 60 | 2 | 1,1-dimethoxycyclohexane (8,9) |
| 15 | Methyl Crotonate (64) | " | 3 | Methyl $\beta$, $\beta$-dimethoxy n-butyrate (15,2) |
| 16 | Methyl Methacrylate (150) | " | " | Methyl $\alpha$-metyl-$\beta$, $\beta$-dimethoxy propionate (10,4) |
| 17 | Methacrylonitrile (120) | 50 | 4 | $\alpha$-methyl-$\beta$, $\beta$-dimethoxy propionitrile (17,2) |
| 18 | Methyl Vinyl Ketone (150) | 60 | 3 | 4,4-dimethoxy-2-butanone (12,1) |

EXAMPLES 8-13 AND COMPARATIVE EXAMPLES 2-5

Into the four-necked flask used in Example 1, 20 ml of methanol, 10 ml of methyl acrylate, 50 ml of 1.4-dioxane (i.e. solvent) and the given amount of a catalyst as listed in Table 2 below were charged.

Then, the contents in the flask were maintained at a temperature of approximately 63° C. and, with stirring, air, or air containing, 13% by volume of methyl nitrite, was fed into the flask for 30 minutes at a rate of 100 ml/min.

The results are shown in Table 2 below.

TABLE 2

| No. | Catalyst (m mol) | Feed Gas | Yield of Formylacetic Acid Dimethylacetal (m mol) |
|---|---|---|---|
| Example 8 | PdCl$_2$(0.56) | Air* | 11.5 |
| Example 9 | PdCl$_2$(0.56) + CuCl$_2$(3.72) | " | 8.0 |
| Example 10 | 10 wt % Pd/C (0.56) + CuCl$_2$(3.72) | " | 9.1 |
| Example 11 | 10 wt % Pd/C (0.56) + CuCl$_2$(0.56) | " | 9.3 |
| Example 12 | 10 wt % Pd/C (0.56) + SnCl$_4$(0.46) | " | 9.6 |
| Example 13 | 10 wt % Pd/C (0.56) + FeCl$_3$(1.12) | " | 7.8 |
| Compara- tive 2 | PdCl$_2$(0.56) + CuCl$_2$(3.72) | Air | 2.6 |
| 3 | PdCl$_2$(0.56) + CuCl$_2$(3.72) + Et N$_3$(4.26) | " | 1.1 |
| Example 4 | 10 wt % Pd/C (0.56) | Air* | 0 |
| 5 | Pd (OAC)$_2$(0.56) | " | 0 |

*Containing 13% by volume of methylnitrite

EXAMPLE 19

A glass reaction tube having an inner diameter of 25 mm and a length of 400 mm was packed with 14.5 g (15 ml) of cylindrical PdCl$_2$-CuCl$_2$-$\gamma$-Al$_2$O$_3$ catalysts containing 1.0% by weight of Pd and 1.2% by weight of Cu supported thereon and, further, glass Raschig rings having a diameter of 3 mm were packed on the catalyst layer at a height of 120 mm. This reaction tube was vertically installed and a ring-type electric oven was mounted on the outside of the reaction tube. Thus, the temperature of the inner catalyst layer was maintained at 80° C. Methyl nitrite diluted with nitrogen to a given concentration was fed into the reaction tube from the top thereof, and methanol was fed into the reaction tube from the top thereof by means of a constant rate pump. On the other hand, acrylonitrile was fed into the reaction tube in the form of a vapor from an evaporator in which the acrylonitrile was heated in a constant temperature bath having a temperature of 40° C., together with nitrogen.

The result is shown in Table 4 below.

EXAMPLES 20-23

The reactions were carried out in a manner as described in Example 19, except that the kinds of the catalysts, the reaction temperatures, the compositions of the starting gases, and the space velocities were changed as shown in Table 4 below.

The results are shown in Table 4 below.

COMPARATIVE EXAMPLE 6

The reaction was carried out in a manner as described in Example 19, except that methanol was not used.

The result is shown in Table 4 below.

TABLE 4

| No. | Catalyst (Wt % in terms of Metal) | Reaction Temp (°C.) | Space Velocity (hr) | Composition of Starting Gas (Vol %)* | | | Space Time Yield of Cyanoacet- aldehyde Dimethyl Acetal (g/cat · l · hr) |
|---|---|---|---|---|---|---|---|
| | | | | Acrylonitrile | Methyl Nitrite | Methanol | |
| Example 19 | (1% Pd + 1.2% Cu) —Al$_2$O$_3$ | 80 | 1330 | 29.8 | 17.2 | 18.4 | 23.2 |
| Example 20 | " | 82 | 1160 | 12.9 | " | ' | 14.9 |
| Example 21 | " | " | 1550 | 18.4 | " | 9.2 | 16.2 |
| Example 22 | (2% Pd + 1.2% Cu) —SiO$_2$ | 104 | 1330 | 23.8 | 14.0 | 18.4 | 24.8 |
| Example 23 | (5% Pd + 1.2% Cu) —SiO$_2$ | 110 | " | " | " | ' | 31.4 |
| Comparative Example 6 | (1% Pd + 1.2% Cu) —Al$_2$O$_3$ | 80 | " | " | 15.5 | 0 | 3.4 |

*Balance of nitrogen gas was contained.

EXAMPLE 24

The reaction was carried out in a manner as described in Example 19, except that ethylene was used in lieu of acrylonitrile, the space velocity of the starting gas (ethylene ... 16.7% by volume, methyl nitrite ... 14.5% by volume, methanol ... 18.4% by volume, nitrogen gas ... balance) was changed to 930 hr$^{-1}$, and the reaction temperature was changed to 90° C.

As a result, acetaldehyde dimethylacetal was obtained at a space time yield of 93.1 g/Cat.l.hr.

EXAMPLE 25

A glass reaction tube having an inner diameter of 25 mm and a length of 400 mm was packed with 14.8 g (15 ml) of a cylindrical PdCl$_2$-FeCl$_3$/SiO$_2$ catalyst containing 1.0% by weight of Pd and 1.2% by weight of Fe and having a diameter of 3 mm and a height of 3 mm and, further, with glass Raschig rings having a diameter of 3 mm on the catalyst layer at a packing height of 120 mm. The reaction tube was vertically installed and a ring-type electric oven was mounted on the outside of the reaction tube. Thus, the temperature of the catalyst layer was heated to approximately 80° C.

From the top of the reaction tube, a starting gas mixture containing 18% by volume of ethylene, 14% by volume of methyl nitrite, 14% by volume of oxygen, 15% by volume of nitrogen monoxide and 39% by volume of nitrogen was fed into the reaction tube at a rate of 20.4 l/hr and liquid methanol was fed at a rate of 9 ml/hr (space velocity = 1690/hr). Thus, the reaction was carried out at a temperature of 110° C.

After the reaction tube effluent gas was passed through cooled methanol, the effluent gas was passed through a trap in the constant temperature bath cooled by dry ice-methanol, whereby the reaction products were collected. The collected liquid was analyzed by means of gas chromatography. As a result, the space time yield of acetaldehyde dimethylacetal was 124 g/l.Cat.hr.

EXAMPLES 26–35

The reaction was carried out in a manner as described in Example 25, except that the kinds of catalysts, the reaction temperature, the composition of the starting gas, and the space velocity were changed as shown in Table 5 below.

The result is shown in Table 5 below.

EXAMPLE 36

The reaction was carried out in a manner as described in Example 25, except that, from the top of the reaction tube, a starting gas mixture comprising 15% by volume of ethylene, 10% by volume of methyl nitrite, 18% by volume of nitrogen monoxide, and 47% by volume of nitrogen was fed at a rate of 43 l/hr and liquid methanol was fed at a rate of 9 ml/hr (space velocity = 3200/hr) and the reaction temperature was changed to 155° C. The result is shown in Table 5 below.

TABLE 5

| Example | Catalyst (Wt % in terms of Metal) | Reaction Temperature (°C.) | Space Velocity .hr$^{-1}$) | Space Time Yield of Acetaldehyde Dimethylacetal (g/l · Cat · hr) |
|---|---|---|---|---|
| 25 | (1%) PdCl$_2$—(1.2%) FeCl$_3$/SiO$_2$ | 110 | 1690 | 124 |
| 26 | (1%) PdCl$_2$—(1.2%) FeCl$_3$/SiO$_2$ | 85 | ' | 17 |
| 27 | (1%) Pd(CH$_3$COO)$_2$— (1.2%) Fe$_3$(CH$_3$COO)$_9$— (2%) SnCl$_4$/SiO$_2$ | " | ' | 15.4 |
| 28 | (1%) Pd(NO$_3$)$_2$— (1.2%) FeCl$_3$/SiO$_2$ | 105 | ' | 105 |
| 29 | (1%) Pd(CH$_3$COO)$_2$— (1.2%) FeCl$_3$/SiO$_2$ | " | ' | 95 |
| 30* | (1%) Pd°—(1.2%) Fe(OH)$_3$/SiO$_2$—HCl | 103 | ' | 30 |
| 31 | (2%) Pd°—(1%) Fe(NO$_3$)$_2$.9H$_2$O—(1%) NiCl$_2$/Al$_2$O$_3$ | 95 | ' | 45 |
| 32* | (1%) Pd°—(1.5%) Fe$_2$O$_3$/SiO$_2$—HCl | 101 | ' | 32 |
| 33 | (1%) PdCl$_2$—(1.2%) FeCl$_3$/Al$_2$O$_3$ | 107 | ' | 110 |
| 34 | (1%) PdCl$_2$—(1.2%) FeCl$_3$/SiO$_2$ | 105 | 2200 | 54 |
| 35 | (1%) PdCl$_2$—(1.2%) | 113 | 1050 | 37 |

TABLE 5-continued

| Example | Catalyst (Wt % in terms of Metal) | Reaction Temperature (°C.) | Space Velocity (hr$^{-1}$) | Space Time Yield of Acetaldehyde Dimethylacetal (g/l · Cat · hr) |
|---|---|---|---|---|
| 36 | FeCl$_3$/SiO$_2$ (1%) PdCl$_2$—(1.2%) FeCl$_3$/SiO$_2$ | 155 | 3200 | 164 |

*HCl used was 50 Vol % HCl diluted with N and fed at a rate of 1 ml/min. together with N.

EXAMPLE 37

The reaction was carried out in a manner as described in Example 25, except that, from the top of the reaction tube, a starting gas mixture comprising 18% by volume of cyclohexene, 14% by volume of methyl nitrite, 14% by volume of oxygen, 15% by volume of nitrogen monoxide and 39% by volume of nitrogen was fed at a rate of 20.4 l/hr and liquid methanol was fed at a rate of 9 ml/hr (space velocity=1690/hr) and the reaction temperature was changed to 95° C.

As a result, 1,1-dimethoxy cyclohexane was obtained, as an acetal, at a space time yield of 16.4 g/l.Cat.hr.

EXAMPLE 38

The reaction was carried out in a manner as described in Example 25, except that, from the top of the reaction tube, a starting gas mixture comprising 18% by volume of methyl acrylate, 18% by volume of oxygen, 29% by volume of nitrogen monoxide and 35% by volume of nitrogen was fed at a rate of 16.6 l/hr, gaseous methyl nitrite was fed at a rate of 3 l/hr and liquid methanol was fed at a rate of 9 ml/hr (space velocity=1640/hr) and the reaction temperature was changed to 85° C.

As a result, methyl 3,3-dimethoxy propionate was obtained at a space time yield of 130 g/l.Cat.hr.

EXAMPLE 39

The reaction was carried out in a manner as described in Example 25, except that, from the top of the reaction tube, a starting gas mixture comprising 18% by volume of propylene, 14% by volume of methyl nitrite, 14% by volume of oxygen, 15% by volume of nitrogen monoxide and 39% by volume of nitrogen was fed at a rate of 20.4 l/hr and liquid methanol was fed at a rate of 9 ml/hr (space velocity=1690/hr) and the reaction temperature was changed to 97° C.

As a result, aceton di n-butylacetal was obtained, as an acetal, at a space time yield of 75 g/l.Cat.hr.

EXAMPLE 40

The reaction was carried out in a manner as described in Example 25, except that, from the top of the reaction tube, a starting gas mixture comprising 15% by volume of acrylonitrile, 15% by volume of ethyl nitrite, 18% by volume of ethanol, 11% by volume of oxygen, 16% by volume of nitrogen monoxide and 25% by volume of nitrogen was fed at a rate of 48 l/hr (space velocity=3200/hr) and the reaction temperature was changed to 75° C.

As a result, cyanoacetoaldehyde diethylacetal was obtained, as an acetal, at a space time yield of 33 g/l.Cat.hr.

EXAMPLE 41

The reaction was carried out in a manner as described in Example 25, except that a starting gas mixture comprising 14% by volume of methyl nitrite, 14% by volume of oxygen, 16% by volume of nitrogen monoxide and 56% by volume of nitrogen was fed at a rate of 16.7 l/hr and a methanol solution containing 60% by volume of 1,4-hexadiene was fed at a rate of 25 ml/hr (space velocity=1690/hr).

As a result, 5,5-dimethoxy-2-hexene was obtained, as an acetal, at a space time yield of 24 g/l.Cat.hr.

EXAMPLE 42

The reaction was carried out in a manner as described in Example 25, except that, from the top of the reaction tube, a gas mixture comprising 5% by volume of oxygen and 95% by volume of nitrogen was fed at a rate of 17 l/hr and a n-butanol solution containing 18% by volume of 1-hexene and 22% by volume n-butyl nitrite was fed at a rate of 50 ml/hr (space velocity=1950/hr) and the reaction temperature was changed to 114° C.

As a result, 2,2-dibutoxy hexane was obtained, as an acetal, at a space time yield of 35 g/l.Cat.hr.

EXAMPLE 43

The reaction was carried out in a manner as described in Example 25, except that a starting gas mixture comprising 17% by volume of ethanol, 14% by volume of oxygen, 18% by volume of nitrogen monoxide, 14% by volume of ethyl nitrite, and 35% by volume of nitrogen was fed at a rate of 15.2 l/hr and an ethanol solution containing 20% by volume of ethyl crotonate was fed at a rate of 40 ml/hr (space velocity=1950/hr) and the reaction temperature was changed to 125° C.

As a result, ethyl β,β-diethoxy n-butyrate was obtained, as an acetal at a space time yield of 10 g/l.Cat.hr.

EXAMPLE 44

140 ml of methanol, 10 ml of acrylonitrite and 0.1 g of PdCl$_2$ were charged into a pressure resistant glass autoclave provided with an agitator and, then, the content of the autoclave was heated to a temperature of 64° C. The reaction was carried out, while a nitrogen gas containing 23% by volume of methyl nitrite was introduced into the autoclave at a rate of 200 ml/min. The reaction pressure was maintained at 1 kg/cmG. The reaction was carried out for 60 min. and, then, the reaction product was cooled. The results are shown in Table 6 below.

EXAMPLE 45 AND 46

Reactions were carried out in a manner as described in Example 44, except that the reaction conditions shown in Table 6 were used. The results are also shown in Table 6 below.

TABLE 6

| | Example | 44 | 45 | 46 |
|---|---|---|---|---|
| Reaction Conditions | Methanol (ml) | 140 | 140 | 130 |
| | Acrylonitrile (ml) | 10 | 10 | 20 |
| | PdCL$_2$ (g) | 0.1 | 0.1 | 0.1 |
| | Temp. (°C.) | 63–64 | 90 | 90 |
| | Press. (kg/cm$^2$G) | 1 | 3 | 3 |
| | Period (hr) | 1 | 1 | 1 |

TABLE 6-continued

| | Example | 44 | 45 | 46 |
|---|---|---|---|---|
| | Methyl nitrite (%) | 23 | 24 | 23 |
| | Flow rate (ml/min.) | 200 | 200 | 600 |
| Result | Cyanoacetaldehyde Dimethyl Acetal | 60.4 | 60.0 | 137.4 |

We claim:

1. A process for producing an acetal comprising the steps of:

introducing an olefin, an alcohol, and an ester of nitrous acid into a reaction system; and contacting, in a liquid phase, the olefin, the alcohol, and the ester of nitrous acid in the presence of (a) at least one component selected from the group consisting of platinum group metals and the salts thereof and (b) at least one halide, provided that the presence of said halide (b) is optional if said component (a) contains a halide.

2. The process as claimed in claim 1, wherein said olefin is at least one compound selected from the group consisting of olefins having 2 to 20 carbon atoms.

3. The process as claimed in claim 1, wherein said alcohol is at least one compound selected from the group consisting of alcohols having alkyl, cycloalkyl and aralkyl groups of 1 to 12 carbon atoms.

4. The process as claimed in claim 1, wherein said ester of nitrous acid is at least one compound selected from the group consisting of esters having 1 to 12 carbon atoms.

5. The process as claimed in claim 1, wherein said platinum group metals selected from are palladium, platinum rhodium, rutenium, iridium and osmium.

6. The process as claimed in claim 1, wherein said salts of the platinum group metals selected from are chlorides, nitrates, sulfates, acetates, phosphates and complex salts.

7. The process as claimed in claim 1, wherein the amount of the halides is 0.1 through 10 mol, in terms of an atomic number of a halogen atom, based on the platinum group metal.

8. The process as claimed in claim 1, wherein said process is carried out at a temperature of 20° through 150° C.

9. The process as claimed in claim 1, wherein said process is carried out under a pressure of an atmosphereic pressure to 200 kg/cmG.

10. The process as claimed in claim 1, wherein the amount of the ester is 0.01% by weight or more, based on the amount of the alcohol.

* * * * *